(12) United States Patent
Lindström et al.

(10) Patent No.: US 10,946,164 B2
(45) Date of Patent: Mar. 16, 2021

(54) VALVE CONTROLLED HIGH FREQUENCY OSCILLATORY VENTILATION

(71) Applicant: MAQUET CRITICAL CARE AB, Solna (SE)

(72) Inventors: Stefan Lindström, Haninge (SE); Carl Erik Troili, Danderyd (SE); Magnus Hallbäck, Danderyd (SE)

(73) Assignee: MAQUET CRITICAL CARE AB, Solna (SE)

( * ) Notice: Subject to any disclaimer, the term of this patent is extended or adjusted under 35 U.S.C. 154(b) by 727 days.

(21) Appl. No.: 14/429,922

(22) PCT Filed: Sep. 21, 2012

(86) PCT No.: PCT/SE2012/051003
§ 371 (c)(1),
(2) Date: Mar. 20, 2015

(87) PCT Pub. No.: WO2014/046583
PCT Pub. Date: Mar. 27, 2014

(65) Prior Publication Data
US 2015/0238724 A1 Aug. 27, 2015

(51) Int. Cl.
*A61M 16/20* (2006.01)
*A61M 16/00* (2006.01)
*A61M 16/12* (2006.01)

(52) U.S. Cl.
CPC ...... *A61M 16/204* (2014.02); *A61M 16/0003* (2014.02); *A61M 16/0009* (2014.02);
(Continued)

(58) Field of Classification Search
CPC ............ A61M 16/204; A61M 16/0003; A61M 16/0057; A61M 16/0096; A61M 16/0009;
(Continued)

(56) References Cited

U.S. PATENT DOCUMENTS

| 4,719,910 A | 1/1988 | Jensen |
| 5,092,326 A | 3/1992 | Winn et al. |

(Continued)

FOREIGN PATENT DOCUMENTS

| CN | 1074620 A | 7/1993 |
| GB | 2485417 | 5/2012 |

(Continued)

*Primary Examiner* — Kendra D Carter
*Assistant Examiner* — Victoria Murphy
(74) *Attorney, Agent, or Firm* — Fay Kaplun & Marcin, LLP (57) ABSTRACT

A breathing apparatus provides high frequency oscillatory ventilation [HFO] to a patient by supplying breathing gas to the patient according to an oscillating pressure profile oscillating between a positive pressure and a negative pressure. The breathing apparatus has a patient circuit including an inspiratory line for conveying breathing gas to the patient, and an expiratory line for conveying gas away from the patient, and an inspiration valve for regulating a flow of pressurised breathing gas into the inspiration line, and a control computer that controls the inspiration valve. The control computer operates to cause the oscillating pressure profile by controlling the inspiration valve to oscillate between a top flow position in which the flow of breathing gas through the inspiration valve assumes a top flow value, and a minimum flow position in which the flow through the inspiration valve assumes a minimum flow value.

24 Claims, 5 Drawing Sheets

(52) U.S. Cl.
    CPC .... *A61M 16/0057* (2013.01); *A61M 16/0096* (2013.01); *A61M 16/205* (2014.02); *A61M 16/12* (2013.01); *A61M 2016/0021* (2013.01); *A61M 2016/0027* (2013.01); *A61M 2016/0036* (2013.01); *A61M 2016/0039* (2013.01); *A61M 2016/0042* (2013.01); *A61M 2205/3334* (2013.01); *A61M 2205/52* (2013.01)

(58) Field of Classification Search
    CPC ........... A61M 16/205; A61M 2205/52; A61M 2205/3334; A61M 2016/0042; A61M 2016/0027; A61M 16/12; A61M 2016/0036; A61M 2016/0021; A61M 2016/0039
    See application file for complete search history.

(56) References Cited

U.S. PATENT DOCUMENTS

| | | | |
|---|---|---|---|
| 5,373,842 A | 12/1994 | Olsson et al. | |
| 6,708,690 B1 * | 3/2004 | Hete | A61M 16/0096 128/204.18 |
| 7,770,580 B2 | 8/2010 | Kruger et al. | |
| 2001/0020473 A1 | 9/2001 | Bennarsten | |
| 2008/0178880 A1 * | 7/2008 | Christopher | A61M 16/0051 128/204.23 |
| 2008/0245366 A1 | 10/2008 | Lee | |

FOREIGN PATENT DOCUMENTS

| | | | | |
|---|---|---|---|---|
| GB | 2485417 A | * | 5/2012 | ........... A61M 16/20 |
| WO | 2011/073839 | | 6/2011 | |
| WO | WO-2012/085792 A2 | | 6/2012 | |

* cited by examiner

VALVE CONTROLLED HIGH FREQUENCY OSCILLATORY VENTILATION

BACKGROUND OF THE INVENTION

Field of the Invention

The present invention relates to a breathing apparatus, method, and a computer program for providing high frequency oscillatory ventilation to a patient.

High frequency oscillatory ventilation (HFO or HFOV) is normally used to deliver small tidal volumes of breathing gas to neonatal patients who cannot be adequately ventilated using conventional ventilation. During inspiration, an overpressure is generated in the breathing circuit of the ventilator to push the breathing gas into the patient, and, during expiration, an underpressure in the breathing circuit serves to pull gas out of the airways of the patient. The application of a pressure profile oscillating between a positive and a negative pressure in relation to surrounding pressure (atmospheric pressure) makes both inspiration and expiration "active", which minimizes the risk of gas trapping in the patient.

HFO ventilation is typically carried out in frequency range of 5-20 Hz with a tidal volume that is smaller than, equal to or only slightly larger than the dead space volume, i.e. the volume comprising the airways of the patient and the volume of the tubing system and tracheal tube of the ventilator. Relevant parameters defining the characteristics of the HFO ventilation include MAP (mean airway pressure), the oscillation frequency and the amplitudes of the positive and negative pressure components of the oscillating pressure profile. In this regard it should be noted that MAP, although being an abbreviation of mean airway pressure, is the mean pressure measured at the Y-piece of the breathing circuit, which pressure does not actually correspond to the airway pressure of a patient undergoing HFO ventilation. Also the pressure amplitudes defining the HFO ventilation are measured in the Y-piece.

HFO should not be confused with high frequency ventilation (HFV) which is a ventilation therapy that only employs active inspiration. In contrast to HFO ventilation, the oscillating pressure applied to the patient during HFV never falls below atmospheric pressure. Thus, whilst HFO involves active inspiration and expiration, HFV only involves active inspiration.

Various techniques are used by HFO ventilators according to prior art to generate the oscillating and typically sinusoidal pressure profile applied to the patient.

For example, there are HFO ventilators that employ piston oscillators to generate the oscillating pressure profile. In piston-based HFO ventilators the piston typically acts on a diaphragm to cause the diaphragm to move back and forth within the diaphragm housing. By having one side of the diaphragm in fluid communication with a gas source and the airways of the ventilated patient, breathing gas with an oscillating pressure profile can be delivered to the patient. Such a piston-based HFO ventilator is known from U.S. Pat. No. 4,719,910.

Other HFO ventilators employ loudspeaker-technique to generate the oscillating pressure profile. Such HFO ventilators are disclosed e.g. in U.S. Pat. Nos. 4,805,612 and 6,085,746.

Yet other HFO ventilators use ejectors, sometimes referred to as jet venturi systems, to generate at least the negative pressure of the oscillating pressure profile, i.e. to provide at least for active expiration of the patient. This is achieved by blowing gas in the expiratory line of the ventilator away from the patient so as to create a negative pressure in the expiratory line, which negative pressure serves to pull gas out of the airways of the patient. In some HFO ventilators, ejectors are used also to create the positive pressure of the oscillating pressure profile by blowing gas in the inspiratory line of the ventilator towards the patient. In other HFO ventilators, the positive pressure is generated through regulation of an inspiration valve of the ventilator whilst the negative pressure is generated by means of an ejector in the expiration line.

Different types of HFO ventilators are further described in the background of U.S. Pat. No. 7,770,580, relating to a HFO ventilator having regulating means for regulating at least one of the amplitude and the oscillation frequency of the respiratory pressure on the basis of the tidal volume applied to the patient.

There are several drawbacks associated with HFO ventilators according to prior art. Piston and loudspeaker based HFO ventilators are sometimes noisy due to the high frequency movement of the piston or diaphragm. Ejector based HFO ventilators are sometimes incapable of generating an underpressure that is sufficient to fully support active expiration by the patient. Furthermore, the need for oscillation generators in form of pistons, loudspeakers or ejectors increases the cost and complexity of the ventilators

SUMMARY OF THE INVENTION

It is an object of the invention to eliminate or at least to mitigate one or more of the above mentioned drawbacks associated with ventilators for providing high frequency oscillatory (HFO) ventilation according to prior art.

This object is achieved by a breathing apparatus for providing HFO ventilation to a patient, as defined by claim 1 in the appended set of claims.

It is also achieved by an associated method and computer program according to claims 12 and 22, respectively.

The invention is based on the discovery that a complete or nearly complete and sufficiently quick interruption of a sufficiently high flow of breathing gas may be used to generate the negative pressure components of an oscillating pressure profile suitable for use in HFO ventilation. This is due to the fact that the kinetic energy of the breathing gas mass can be used to generate an underpressure in the breathing apparatus tubing that is sufficient to provide for active expiration of a patient connected to the breathing apparatus.

Through fast regulation of an inspiration valve of a breathing apparatus according to the invention, pulses of breathing gas are generated and transmitted towards the patient through an inspiratory line of the breathing apparatus. The injection of breathing gas into the inspiratory line generates a pressure increase in the tubing system, followed by a pressure decrease due to the deceleration of the breathing gas flow when the inspiration valve is rapidly closed. With a sufficiently high top flow rate and sufficiently fast closing of the inspiration valve, the deceleration of the flow rate generates a negative pressure (i.e. a sub-atmospheric pressure) behind the breathing gas pulse. The inertia of the breathing gas pulse makes it propagate through the inspiratory line towards a proximal tubing of the breathing apparatus, including a patient connector connecting the patient to the inspiratory line and an expiratory line. As the pressure increases in the tubing system, gas will be pushed into the airways of the patient and so provide for active inspiration. The kinetic energy of the breathing gas pulse will make at least a part of the pulse propagate into the expiratory line. If, by this time, no new flow of breathing gas has been allowed into the inspiration line, the negative pressure behind the gas pulse, or the remains of the gas pulse, will pull gas out from the airways of the patient and so provide for active expiration. The patient will hence be subjected to active inspiration as the breathing gas pulse propagates towards the patient in the inspiratory line of the breathing apparatus, and to active expiration as the breathing gas pulse propagates away from the patient in the expiratory line of the breathing apparatus. It has been found that negative pressure components in the magnitude of −50 cmH$_2$O can be generated with no oscillating components other than the oscillating inspiration valve.

By generating a pulse train of well-defined breathing gas pulses with high kinetic energy, true HFO ventilation with active inspiration and active expiration can thus be provided by no other means than an oscillating inspiration valve with a sufficiently fast closing mechanism, oscillating between an open position allowing a sufficiently high flow of breathing gas through the inspiration valve, and a closed or nearly closed position at which the flow through the inspiration valve is zero or nearly zero. The negative pressure required to provide for active expiration is generated only by use of the kinetic energy of the breathing gas pulses injected through the inspiration valve.

Thus, according to one aspect of the invention, a breathing apparatus, such as a ventilator or an anaesthesia machine, for providing HFO ventilation to a patient is provided. The breathing apparatus is configured to provide the HFO ventilation by supplying breathing gas to the patient according to an oscillating pressure profile oscillating between a positive and negative pressure in relation to surrounding (atmospheric) pressure. The breathing apparatus comprises an inspiratory line for conveying breathing gas to the patient, an expiratory line for conveying gas away from the patient, and an inspiration valve for regulating a flow of pressurised breathing gas into the inspiratory line. The breathing apparatus further comprises a control unit for controlling the inspiration valve, which control unit is configured to generate the oscillating pressure profile by controlling the inspiration valve to oscillate between a top flow position in which the flow of breathing gas through the inspiration valve assumes a top flow rate, and a minimum flow position in which the flow through the inspiration valve assumes a minimum flow rate that is zero or nearly zero.

Thus, in contrast to HFO ventilators according to prior art, both the positive pressure components and the negative pressure components of the oscillating pressure profile are generated by an oscillating inspiration valve.

As previously mentioned there are HFO ventilators according to prior art that use an inspiration valve of the ventilator to generate the positive pressure components of the pressure profile. However, these HFO ventilators all use ejectors or other suitable devices to generate the negative pressure components of the pressure profile. For one or more of the following three reasons, no negative pressure components are or could be generated by the oscillation of the inspiration valve in these HFO ventilators according to prior art:

First, the top flow rate is not sufficiently high in known HFO ventilators. In order for the inertia of the breathing gas pulses to be high enough to generate a negative pressure capable of pulling gas out of the airways of the patient, the top flow rate of the breathing gas through the inspiration valve must be sufficiently high. The HFO ventilators according to prior art typically deliver top flows of approximately 30 lpm. The HFO ventilator according to the present invention is capable of delivering flows up to 180 lpm, which makes the gas pulses injected through the inspiration valve carry approximately 36 times the kinetic energy carried by corresponding gas pulses injected through the inspiration valves of these known HFO ventilators.

Second, the regulation of the inspiration valve is too slow in known HFO ventilators. Besides the fact that the top flow through the inspiration valve has to be sufficiently high, it has to be interrupted very abruptly to generate a sufficient negative pressure to provide for active expiration of the patient. This means that the regulation speed and in particular the closing speed of the inspiration valve must be very high. The HFO ventilators according to prior art are not able to produce the negative pressure components required for active expiration of the patient since they are not able to bring the flow of breathing gas down from the top flow rate to zero or nearly zero flow fast enough. Furthermore, as the inspiration valve oscillates with a frequency corresponding to the frequency of the HFO ventilation, the inspiration valve would preferably have to be able go from a closed or nearly closed position to an open position allowing a sufficiently high top flow rate, and back again, up to at least 20 times per second (corresponding to a HFO ventilation of 20 Hz). The inspiration valves and their control mechanisms in the HFO ventilators according to prior art are too slow to oscillate between these two extreme positions at the required frequency.

Third, the bias flow is typically too high in known HFO ventilators. Not only does the top flow rate and the regulation of the inspiration valve be sufficiently high in order to generate negative pressure near the patient in the patient circuit. Also, the flow (bias flow) through the inspiration valve when in its most closed position has to be small enough, since the deceleration (i.e. the decrease in flow per time unit) has to be high enough. In known HFO ventilators, the bias flow is typically around 3 lpm or more, which, given their top flow rates and their closing speeds of the inspiration valve is too much to yield any negative pressure in the patient circuit.

As understood from above, both the top flow rate, the minimum flow rate, and the rate of change in flow from the top flow rate to the minimum flow rate have impact on the magnitude of the negative pressure arising behind the breathing gas pulses. The control unit of the inventive breathing apparatus preferably controls the inspiration valve to go from the top flow position to the minimum flow position at a speed resulting in a mean rate of change in flow from the top flow rate to the minimum flow rate of at least 7200 lpm/s (corresponding to a flow fall time of 25 ms from 180 lpm to zero flow), more preferably at least 12000 lpm/s, and even more preferably at least 18000 lpm/s (corresponding to a flow fall time of 10 ms from 180 lpm to zero flow). At a closing speed resulting in a mean rate of change of 18000 lpm/s, a top flow rate of 30 lpm is sufficient to generate a negative pressure that is low enough to provide for active expiration. Preferably, however, to obtain a decent MAP (Mean Airway pressure) and pressure amplitude coverage in the relevant frequency range of at least 5-20 Hz, the top flow rate should be at least 60 lpm, and even more preferably at least 120 lpm. Furthermore, the minimum flow rate (bias flow) should not be more than 4 lpm, and preferably not more than 1 lpm.

In the following, when talking about opening and closing the inspiration valve, it should be appreciated that opening the inspiration valve means to open the valve from the minimum flow position to the top flow position, and that closing the inspiration valve means to bring the valve from the top flow position to the minimum flow position. As understood from the above discussion, the minimum flow position is a completely closed position in which the flow through the inspiration valve is zero or a nearly closed position in which the flow through the inspiration valve is below 4 lpm and preferably below 1 lpm.

Thus, in order to provide the proposed HFO ventilation at frequencies of 20 Hz or more, the inspiration valve of the breathing apparatus should be able to go from its most open "top flow position" to a fully or nearly closed position very fast. A commercially available (non-HFO) ventilator having an inspiration valve and a valve control mechanism that fulfil the above mentioned requirement is the SERVO-i ventilator developed and manufactured by Maquet Critical Care AB. It is contemplated that the invention can be implemented by adapting conventional ventilators having sufficiently fast inspiration valves to provide the proposed HFO ventilation, such as the SERVO-i ventilator. Adaption to HFO ventilation can be made by installing a suitable computer program on a non-volatile memory of the control unit of the ventilator, which computer program transforms the conventional ventilator to a HFO-enabled ventilator by causing it to perform the method described herein when the computer program is executed by a processing unit of the control unit. No hardware modifications of the SERVO-i ventilator are required to provide the proposed HFO ventilation. Preferably, however, the check valves normally arranged in the proximal ends of the inspiratory and expiratory lines are removed to avoid noise otherwise caused by these check valves during HFO ventilation.

To further increase the effect of active expiration, the breathing apparatus preferably comprises means for preventing or at least limiting a reverse flow of gas in the expiratory line, i.e. a flow of gas towards the patient. The negative pressure arising behind each gas pulse has the effect of decelerating the gas pulse when propagating through the tubing system. If the inertia of the gas pulse becomes zero while there is still some negative pressure in the expiratory line, a reverse flow (back suction) counteracting the active expiration of the patient may occur in the expiratory line. By preventing such a reverse flow, the active expiration of the patient can be prolonged.

Preferably, the reverse flow is prevented by means of an expiration valve arranged in a distal end of the expiratory line. Such expiration valves are used in most breathing apparatuses of today. In order to prevent reverse flow in the expiratory line during HFO ventilation, the expiration valve may be configured to close before the negative pressure in the expiration line causes a reverse flow. Preferably, the expiration valve is an electro-mechanical one-way expiration valve designed to allow a flow of gas in the direction away from the patient while preventing a flow of gas in the opposite direction, as long as no control current is applied to the valve. When a control current is applied to the valve, it is kept closed no matter the direction of flow, and the closing force is dependent on the magnitude of the control current. Such an expiration valve will automatically prevent reverse flow through the expiration valve while having the further advantage of allowing the control unit of the breathing apparatus to adjust the closing force of the expiration valve in dependence of the pressure in the patient circuit to prevent leakage of gas through the expiration valve during the inspiration phases of the HFO ventilation. This may be achieved by applying a control current to the expiration valve having a magnitude that increases during the duration of each inspiration phase to compensate for the increasing pressure in the patient circuit.

A reverse flow in the expiratory line could also be prevented by one or more passive components, such as a mechanical one-way valve arranged in the expiration line. It has also been shown that a sufficient limitation of reverse flow in the expiration line can be achieved by increasing the length of the expiratory line of the breathing apparatus providing the HFO ventilation. Thus, according to yet another embodiment of the invention, the means for preventing or limiting a reverse flow of gas in the expiration line comprises a length of tubing extending the length of the expiratory line of the breathing apparatus.

When the breathing apparatus comprises an electronically controlled expiration valve, the control unit is preferably configured to further improve the effect of the HFO ventilation by synchronously controlling the inspiration valve and the expiration valve. In a preferred embodiment of the invention, the control unit is configured to control the inspiration valve and the expiration valve such that they are out of phase, meaning that they are not opened and closed simultaneously.

The expiration valve is kept closed when the inspiration valve is opened. Preferably, the expiration valve is maintained closed also for a short period of time after the inspiration valve is closed. The time delay between closing of the inspiration valve and opening of the expiration valve is herein referred to as the expiratory delay. This has the effect of increasing the fresh gas content delivered to the patient during each inspiration as a delayed opening of the expiration valve will increase the flow of breathing gas into a common line of a patient connector connecting the inspiratory line and the expiratory line with the patient, and further onto the airways of the patient. The expiratory delay is preferably selected such that each breathing gas pulse causes a sufficient volume of breathing gas to flow into the airways of the patient during each period of the HFO ventilation.

As mentioned above, a controllable expiration valve may also serve to prevent reverse flow in the expiratory line. If designed as an electro-mechanical one-way valve as described above, it will automatically prevent reverse flow in the expiratory line. However, depending on the design of the expiration valve, a small reverse flow having a negative impact on the active expiration of the patient may still appear, for example if there is a small gap between a membrane and a valve seat of the valve when no control current is applied. Therefore, it may be desired to actively close the expiration valve by applying a control current to the valve near the end of the expiration phases, while there is still some negative pressure in the expiratory line. This means that the expiration valve may be actively controlled to close some time before initiating a subsequent inspiration phase by opening the inspiration valve.

Thus, the control of the inspiration and expiration valves may further comprise another time delay, herein referred to as the inspiratory delay, between the closing of the expiration valve and the opening of the inspiration valve.

The optimal inspiratory and expiratory delay times depend mainly of the length of tubing of the patient circuit, the frequency of the HFO ventilation and the characteristics of the ventilated patient. According to one embodiment of the invention, one or both of the inspiratory delay time and the expiratory delay time may be set by an operator of the ventilator or be automatically set by the control unit of the ventilator by performing a pre-use check in which one or both of said delay times are optimised to provide HFO ventilation to the patient according to a predetermined pressure profile. In such a pre-use check, the ventilator may be adapted to compare measured pressure in the patient circuit with pressures given by the predetermined pressure profile and adjust the inspiratory and/or expiratory delay times to minimize any deviation therebetween. Preferably, the ventilator is further adapted to automatically adjust one or both of the inspiratory and expiratory delay times during ongoing HFO ventilation to ensure that the delivered pressure profile does not deviate from the desired predetermined pressure profile, e.g. by repetitively comparing measured pressure values with the desired pressure profile and adjust one or both time delays to compensate for any deviation.

Further advantageous aspects of the invention will be described in the detailed description following hereinafter.

BRIEF DESCRIPTION OF THE DRAWINGS

The present invention will become more fully understood from the detailed description provided hereinafter and the accompanying drawings which are given by way of illustration only. In the different drawings, same reference numerals correspond to the same element.

DETAILED DESCRIPTION

Figure 1:
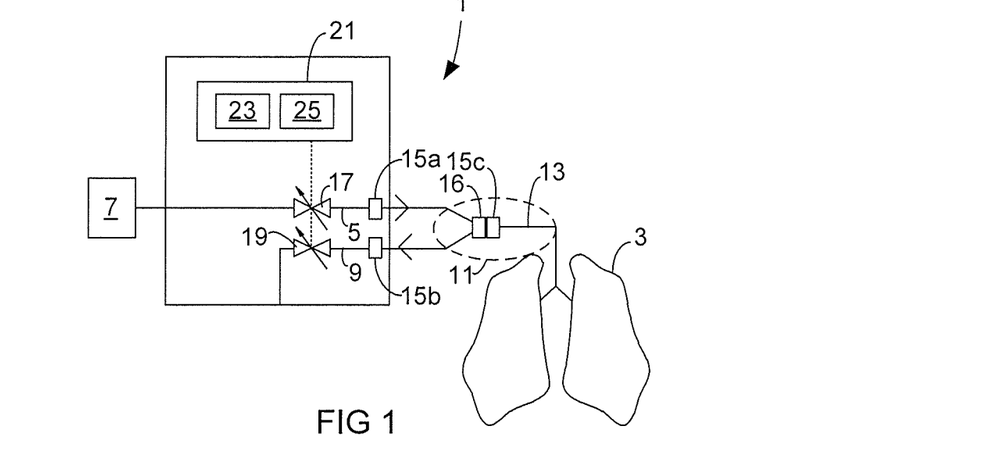
FIG. 1 illustrates a breathing apparatus for providing HFO ventilation to a patient, according to an exemplary embodiment of the invention.

FIG. 1 illustrates a breathing apparatus 1 for providing high frequency oscillatory (HFO) ventilation to a patient 3, according to an exemplary embodiment of the invention. The breathing apparatus 1 is a ventilator comprising an inspiratory line 5 for conveying pressurised breathing gas from at least one gas source 7 to the patient 3, and an expiratory line 9 for conveying expiration gas away from the patient 3 to atmosphere or a scavenging system (not shown). The inspiratory line 5 and the expiratory line 9 are connected to each other and to the patient 3 via a patient connector 11 comprising a common line 13 for conveying the breathing gas and the expiration gas to and from the patient. The patient connector 11 further comprises a so called Y-piece connecting the inspiratory line 5 and the expiratory line 9 with the common line 13. The inspiratory line 5, expiratory line 9, and the patient connector 11 together form a patient circuit of the breathing apparatus 1.

The breathing apparatus 1 may further comprise at least one flow sensor 15a-c for measuring the flows in the inspiratory line 5, the expiration line 9, and/or the patient connector 11. Furthermore, the breathing apparatus may comprise one or more pressure sensors for measuring the pressure in the patient circuit. In this embodiment, the breathing apparatus comprises at least one pressure sensor 16 arranged in the Y-piece of the patient connector 11.

Furthermore, the breathing apparatus 1 comprises a controllable inspiration valve 17 for regulating the flow of breathing gas supplied to the patient 3 via the inspiratory line 5, and a controllable expiration valve 19.

The inspiration valve 17 and the expiration valve 19 are controlled by a control unit 21 of the breathing apparatus 1 based on preset parameters input to the breathing apparatus by an operator thereof, and/or measured parameters measured by various sensors of the breathing apparatus, such as the flow sensors 15a-c and the pressure sensor 16. The control unit 21 comprises a non-volatile memory 23 storing a computer program that causes the control unit 21 to control the inspiration valve 17 and expiration valve 19 according to the principles described below, when executed by a processing unit 25 of the control unit 21. Unless stated otherwise, all steps of the method described hereinafter are performed by the control unit 21 of the breathing apparatus 1 through execution of the computer program.

Although only one gas source 7 is shown in FIG. 1 it should be appreciated that the breathing apparatus 1 may be connected to multiple gas sources for providing a breathing gas mixture comprising multiple gas components to the patient 3. As common in the art, the breathing apparatus may therefore comprise a gas mixing tank upstream of the inspiration valve 17, or it may comprise a plurality of inspiration valves, each arranged to control the flow of a respective gas component into the inspiration line 5. The gas source 7 may for example comprise one or more wall outlets delivering pressurised air and/or oxygen, commonly available in hospital environments.

Figure 2:
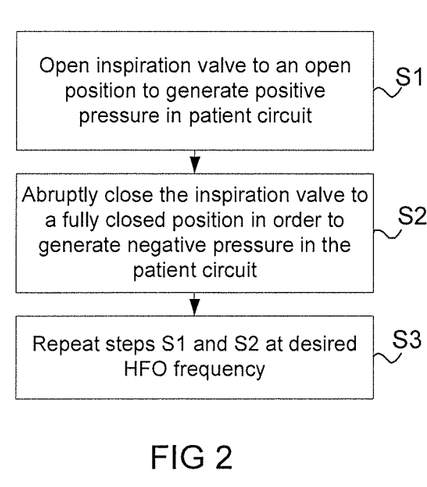
FIG. 2 is a flow chart illustrating a method for providing HFO ventilation to a patient 3, according to an exemplary embodiment of the invention.

FIG. 2 illustrates a method for providing HFO ventilation to a patient by means of the breathing apparatus 1, according to an exemplary embodiment of the invention.

In a first step S1, the inspiration valve 17 of the breathing apparatus 1 is opened to a top flow position at which a pressurised flow of breathing gas through the inspiration valve 17 reaches a top flow rate.

In a second step S2, the inspiration valve 17 is abruptly closed by bringing the inspiration valve 17 from said top flow position to a minimum flow position at which the flow through the inspiration valve 17 is limited to a minimum flow rate that is zero or nearly zero.

The opening of the inspiration valve 17 in step S1 generates a positive pressure in the patient circuit, providing for active inspiration by the patient 3. The top flow rate, the minimum flow rate and the closing speed of the inspiration valve 17 are selected such that the abrupt closing of the inspiration valve 17 in step S2 generates a negative pressure in the patient circuit, following the positive pressure caused by the opening thereof, as will be described below with reference to FIGS. 3A-3G.

In a third step S3, the steps S1 and S2 are repeated at a frequency corresponding to the desired frequency of the HFO ventilation. The breathing apparatus 1 is adapted to provide HFO ventilation at least in the frequency range of 5-20 Hz, and preferably in the wider range of 5-50 Hz, meaning that the breathing apparatus is capable of repeating steps S1 and S2 at least 20 times per second, and preferably up to 50 times per second.

The oscillation of the inspiration valve 17 between the top flow position and the minimum flow position causes the pressure in the patient circuit 5, 9, 11 of the breathing apparatus 1 to oscillate, during each period of the HFO ventilation, between a positive pressure serving to push gas into the airways of the patient 3, and a negative pressure serving to pull gas out of the airways of the patient 3. Thereby, the breathing apparatus 1 is capable of providing HFO ventilation with active inspiration and active expiration without the use of any oscillating parts except for the oscillating inspiration valve 17.

The inspiration valve 17 is controlled by the control unit 21 to deliver breathing gas according to the oscillating pressure profile by applying a control current to the inspiration valve 17, making the inspiration valve 17 oscillate between the top flow position and the minimum flow position in accordance with the frequency of the control current. The control current may for example have a sinusoidal wave form, a square wave form, a triangle wave form or a sawtooth waveform. A square wave form is advantageous in that it provides the fastest opening and closing speeds of the inspiration valve 17. However, the overtones of a square wave control current makes the operation of the HFO ventilator noisy. Therefore, the control current is preferably selected to have a near square wave form, e.g. by being a mixture of a square wave and a sine wave.

Typically, the operator of the breathing apparatus 1 selects a desired oscillating pressure profile to be provided to the patient by setting a desired oscillation frequency and MAP (Mean Airway Pressure) for the HFO ventilation, e.g. in the ranges of 5-20 Hz and 0-35 mbar, respectively. Furthermore, the breathing apparatus 1 may be configured to allow the operator to set a desired amplitude for the pressure profile. The range of possible pressure amplitudes depends on the set frequency and MAP as well as the characteristics of the breathing circuit and, therefore, the range of selectable amplitudes are preferably limited by the control unit 21 based on the set frequency, the set MAP, and the characteristics of the breathing apparatus. Based on the set frequency, the set MAP, and additionally the set pressure amplitude, the control unit 21 automatically determines a flow profile resulting in the desired pressure profile, and adapts the control current applied to the inspiration valve so as to obtain the determined flow profile.

The pressure in the patient circuit is typically sampled during HFO ventilation, e.g. by means of the pressure sensor 16 in the patient connector 11. If the measured pressure deviates from the desired pressure profile, the control current and hence the profile of the flow of breathing gas through the inspiration valve 17 is adjusted accordingly. Preferably, the control unit 21 is arranged to compare the measured pressure with preset control values, and, if necessary, adjust the control current and hence the oscillatory movement of the inspiration valve 17 based on said comparison. Preferably, the sampling and comparison is performed in each period of the HFO ventilation, which means that the flow profile can be adjusted on a breath-by-breath basis to ensure that the patient is always subjected to a pressure following the desired pressure profile. As will be described below, in other embodiments of the invention, an actively controlled expiration valve can be used to enhance the active expiration of the patient. In such embodiments, also the regulation of the expiration valve can be adjusted to compensate for deviations between the measured pressure and the desired pressure profile.

FIGS. 3A-3G illustrates in a simplified manner the effects of the above method steps on the pressure and flow in the patient circuit of the breathing apparatus 1. In FIGS. 3A-3G, more densely dotted areas of the patient circuit indicate a higher pressure than the pressure in less densely dotted areas of the patient circuit, while arrows are used to indicate whether gas is pushed into or drawn out from the patient 3 at the different points in time represented by the respective drawings.

Figure 3A:
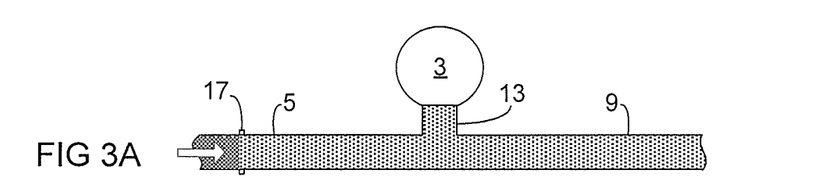
FIGS. 3A-3G illustrate in a simplified manner the pressure and flow development in a patient circuit of a breathing apparatus providing HFO ventilation according to an exemplary embodiment of the invention.
Figure 3B:
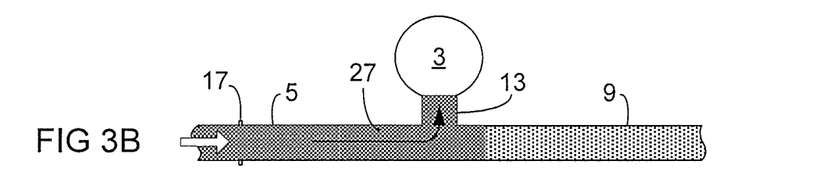

The opening of the inspiration valve in step S1 makes pressurised breathing gas from one or more gas sources 7 (FIG. 1) flow into the inspiratory line 5, as illustrated in FIGS. 3A and 3B. The supply of breathing gas causes a pressure increase in the patient circuit.

As illustrated by the arrow in FIG. 3B, this pressure increase causes a forced flow of breathing gas into the common line 13 of the patient connector 11 and onto the airways of the patient 3, and so provides for active inspiration of the patient. After some time, as illustrated in FIG. 3C, the pressure is increased in the entire patient circuit, 5, 9, 11, and breathing gas continues to flow into the patient 3.

Figure 3C:
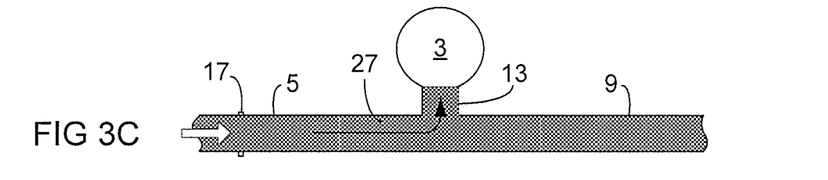
Figure 3D:
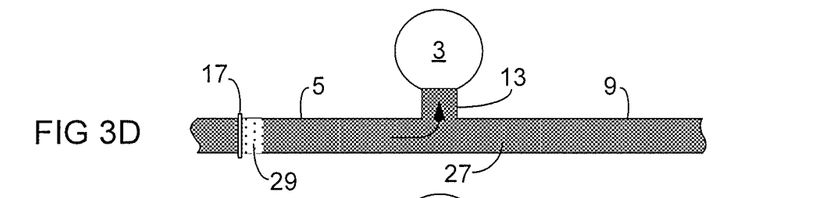

As illustrated in FIG. 3D, the abrupt closing of the inspiration valve 17 in step S2 cuts off or at least abruptly decelerates the flow of breathing gas and so generates a breathing gas pulse 27 that propagates through the inspiratory line 5 due to the inertia of the breathing gas.

The rapid deceleration of the breathing gas flow rate caused by the abrupt closing of the inspiration valve 17 causes a negative pressure, i.e. a sub-atmospheric pressure, to develop behind the breathing gas pulse 27. The negative pressure field behind the breathing gas pulse 27 is denoted by reference numeral 29. Here, the inspiration valve 17 is closed at a point in time occurring between the points in time illustrated in FIGS. 3C and 3D.

When the pressure increases in the patient circuit, gas flows into the common line 13 of the patient circuit and into the airways of the patient, as indicated by the arrow in FIGS. 3B-3D. The gas entering the airways of the patient 3 in each period of the HFO ventilation typically but not necessarily includes at least some of the gas in the breathing gas pulse 27 injected into the inspiratory line 5 via the inspiration valve 17 during the same period. The volume of gas entering the airways of the patient 3 during each period of the HFO ventilation is typically much smaller than the gas volume of the breathing gas pulse 27.

Figure 3E:
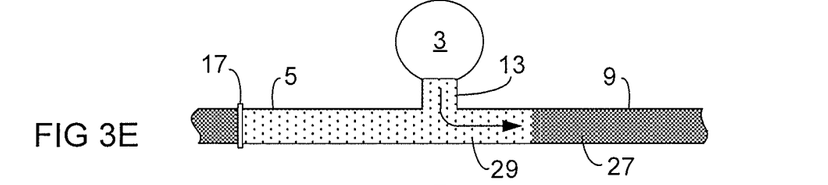
Figure 3F:
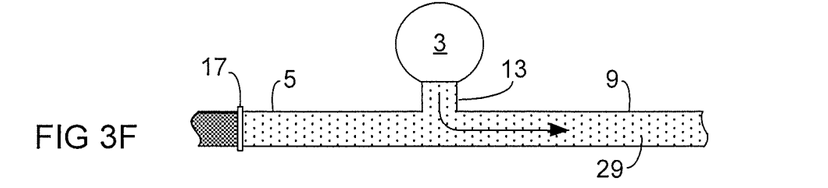

As illustrated in FIGS. 3E and 3F, some of the breathing gas pulse 27 and the ensuing negative pressure field 29 will propagate into the expiratory line 9 of the patient circuit, where the negative pressure will cause gas to be pulled out of the airways of the patient 3 and the common line 13 to level out the pressure in the patient circuit. The negative pressure will hence provide for active expiration of the patient 3.

Figure 3G:
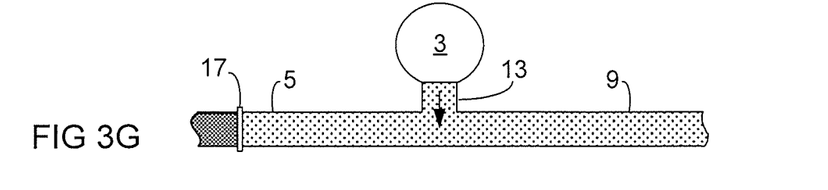

As illustrated in FIG. 3G, the gas flow from the airways of the patient 3 will gradually level out the negative pressure in the patient circuit. At some point in time, the negative pressure will be leveled out, whereby the active expiration phase is over and a new period of the HFO ventilation commencing with an active inspiration phase can be initiated by once again opening the inspiration valve 17 (FIG. 3A). It should, however, be appreciated that a new inspiration phase may be initiated by opening the inspiration valve 17 before the negative pressure field 29 in the patient circuit is completely leveled out by gas flowing from the airways of the patient 3. The important thing in order for the patient 3 to experience active expiration is that a negative pressure of a magnitude that is sufficient to pull at least a small volume of gas out of the patient's airways is generated in the patient circuit due to the abrupt closing of the inspiration valve 17, and that the negative pressure is given at least some time to pull gas out of the airways of the patient before injecting a new pulse of breathing gas through the inspiration valve 17.

Figure 4:
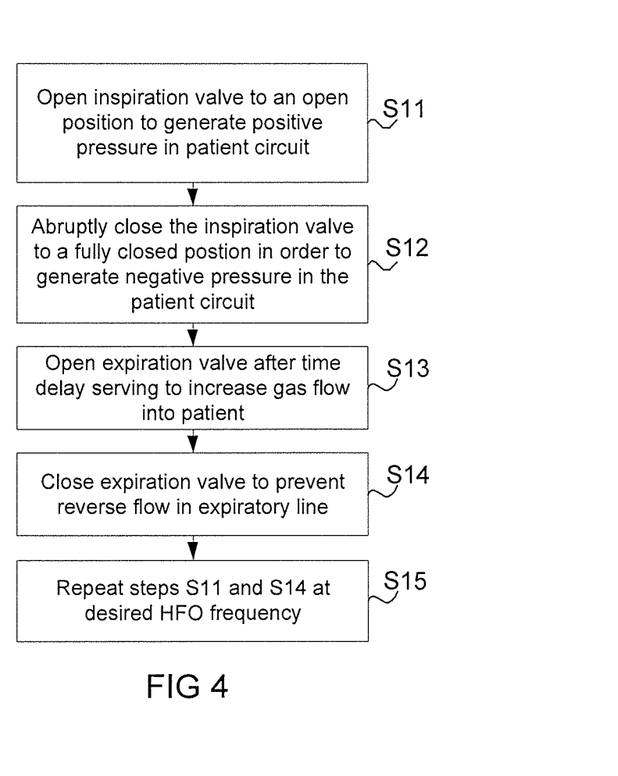
FIG. 4 is a flow chart illustrating a method for providing HFO ventilation to a patient 3, according to an exemplary embodiment of the invention.

FIG. 4 illustrates a method for providing HFO ventilation to a patient by means of the breathing apparatus 1, according to another exemplary embodiment of the invention. The difference compared to the method in FIG. 2 is that a controllable expiratory valve 19 of the breathing apparatus 1 is used to enhance the effect of active expiration.

The first steps S11 and S12 correspond to the steps S1 and S2, respectively, in FIG. 2.

In a third step S13, the expiration valve 19 (FIG. 1) (which is closed when opening the inspiration valve in step S11) is opened. Preferably, the closing of the inspiration valve 17 in step S12 and the opening of the expiration valve 19 is not made simultaneously. Instead, the opening of the expiration valve 19 is preferably delayed by a certain delay time, hereinafter referred to as the expiratory delay. Keeping the expiratory valve 19 closed for a certain time after having closed the inspiration valve 15 causes more of the fresh gas in the breathing gas pulse 27 to flow into the common line 13 of the patient connector 11 and into the airways of the patient 3 than if the expiration valve 19 would have been opened when the inspiration valve 17 is closed. The opening of the expiration valve 17 causes at least some of the breathing gas pulse 27 and the ensuing negative pressure field 29 to propagate into the expiratory line 9 where the negative pressure serves to pull gas out of the airways of the patient 3, and so serves to initiate an active expiration phase. The expiratory time delay is preferably in the range of 0-10 ms, depending on the length of the tubing of the patient circuit, the frequency of the HFO ventilation, and the characteristics of the patient.

In a fourth step S14, the expiration valve 19 is closed. The expiration valve 19 is preferably closed near the end of the active expiration phase while there is still some negative pressure in the expiratory line 9. This is made to prevent a reverse flow in the expiratory line 9, i.e. a flow of gas from the distal end of the expiratory line 9 towards the proximal end of the expiratory line. Such a reverse flow would level out the negative pressure in the more proximal parts of the expiratory line 9 and so prevent gas from being pulled out of the airways of the patient 3. The closing of the expiration valve 19 thus has the effect of prolonging the active expiration of the patient 3. The time delay between the closing of the expiration valve 19 near the end of an expiration phase and the opening of the inspiration valve 17 to initiate a subsequent inspiration phase is hereinafter referred to as the inspiratory delay. The inspiratory delay is preferably in the range of 0-50 ms, also depending on the length of the tubing of the patient circuit, the frequency of the HFO ventilation, and the characteristics of the patient.

In a fifth and final step S15, the steps S11-S14 are repeated at a frequency corresponding to the desired frequency of the HFO ventilation.

FIGS. 5A-5G illustrates in a simplified manner the effects of the method steps in FIG. 3 on the pressure and flow in the patient circuit of the breathing apparatus 1. Like in FIGS. 3A-3G, more densely dotted areas of the patient circuit indicate a higher pressure than the pressure in less densely dotted areas of the patient circuit, and arrows are used to indicate whether gas is pushed into or drawn out from the patient 3 at the different points in time represented by the respective drawings.

The only difference between FIGS. 5A-5G and previously described FIGS. 3A-3G is that the expiration valve 19 of the breathing apparatus 1 is used to improve the HFO ventilation as described above with reference to FIG. 4.

Figure 5A:
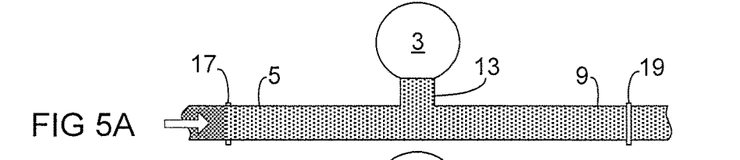
FIGS. 5A-5I illustrate in a simplified manner the pressure and flow development in the patient circuit of a breathing apparatus providing HFO ventilation according to an exemplary embodiment of the invention.
Figure 5B:
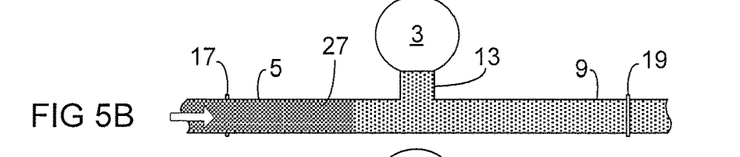
Figure 5C:
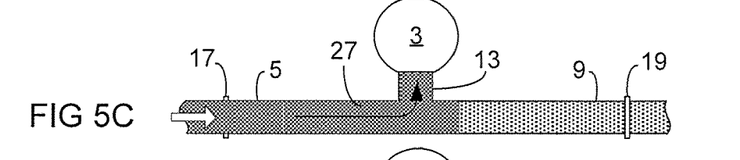
Figure 5D:
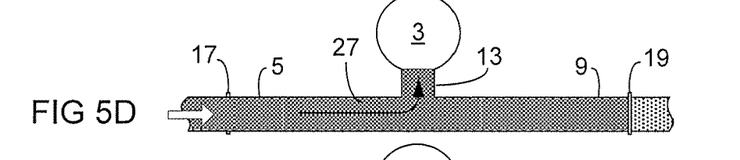
Figure 5E:
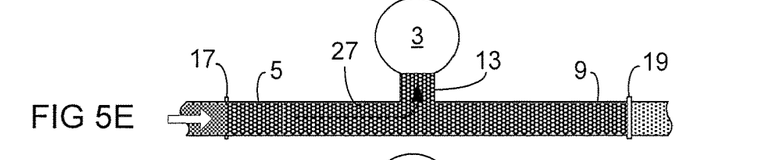

To increase the flow of gas to the patient 3, the expiratory valve 19 is kept closed during an initial part of the inspiration phase, as illustrated by FIGS. 5A-5E. As indicated by FIG. 5E, keeping the expiration valve 19 closed causes continued pressure increase in the patient circuit 5, 9, 11, which in turn causes the pressure to increase also in the lungs of the patient 3. This pressure increase serves to increase both the amplitude and the mean pressure of the oscillating pressure profile.

Figure 5F:
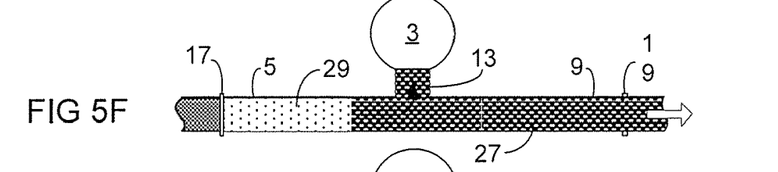
Figure 5G:
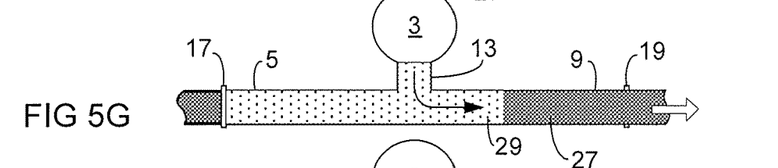

At a point in time between the points in time represented by FIGS. 5E and 5F, the inspiration valve 17 is closed. Then, at a later point in time, represented by FIG. 5F, the expiration valve 19 is opened. The time elapsed between the closing of the inspiration valve 17 and the opening of the expiration valve 19 corresponds to the above mentioned expiratory delay. As mentioned above, the abrupt closing of the inspiration valve 17 decelerates the flow and so causes a negative pressure 29 to arise at the inspiration valve 17 in the patient circuit. As the expiration valve 19 opens, the overall overpressure in the patient circuit makes the breathing gas in the patient circuit accelerate and flow out through the expiration valve 19, whereupon the ensuing underpressure 29 serves to pull out gas from the airways of the patient 3 and so provide for active expiration of the patient 3, as illustrated in FIG. 5G Near the end of the active expiration phase, the expiration valve 19 is closed to prevent reverse flow of gas in the expiratory line 9. This occurs at a point in time represented by FIG. 5H, when there is still some negative pressure 29 in the patient circuit. Thus, the closing of the expiration valve near the end of the active expiration phase serves to trap the underpressure 29 in the patient circuit to make sure that this underpressure is leveled out by gas flowing from the airways of the patient 3, as illustrated in FIG. 5I, instead of by a reverse gas flow in the expiratory line 9.

Figures 5H, 5I:
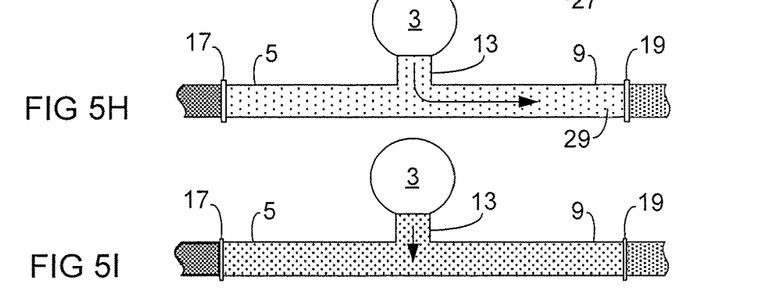

As illustrated in FIGS. 5H and 5I, the expiration valve 19 is closed before the inspiration valve 17 is opened to initiate the subsequent inspiration phase (as illustrated in FIG. 5A). The time elapsed between the closing of the expiration valve 19 during a final phase of an expiration phase (FIG. 5H) and the opening of the inspiration valve (FIG. 5A) initiating a subsequent inspiration phase corresponds to the above mentioned inspiratory delay.

Thus, in this embodiment, the control unit 21 is configured to control the inspiration valve 17 and the expiration valve 19 such that they are out of phase, meaning that they are not opened and closed simultaneously. In this embodiment, there is both an expiratory time delay serving to increase the flow of fresh gas into the patient 3 during the active inspiration phases, and an inspiratory time delay serving to prolong the active expiration phases by preventing reverse flow of gas in the expiratory line 9. These time delays may be set by an operator of the HFO ventilator based on e.g. the length of the tubing of the patient circuit, the set frequency of the HFO ventilation, and the characteristics of the patient. They may also be set and/or adjusted continuously by the control unit 21 based on flow and/or pressure measurements obtained in the patient circuit, e.g. flow and/or pressure measurements obtained by one or more of the flow sensors 15a-15c and/or the pressure sensor 16 (FIG.

1). Preferably, the control unit 21 is configured to automatically adapt the inspiratory and/or expiratory time delays during ongoing HFO ventilation based on such measurements in order to ensure that the oscillating pressure profile follows a desired pressure profile having a desired MAP and acceptable positive and negative pressure amplitudes.

To ensure that the oscillating pressure profile follows the desired pressure profile, the control unit 21 may further be configured to automatically adapt the profile of the flow injected through the inspiration valve 17 during ongoing HFO ventilation. To this end, the control unit 21 may be configured to adapt both the maximum degree of opening of the inspiration valve 17 (i.e. the top flow position of the inspiration valve) and, depending on the type of valve, the opening and/or closing speed of the inspiration valve 17. These parameters may be adjusted by the control unit 21 by adjusting the profile of the control current used to regulate the inspiration valve 17. As mentioned above, the regulation of the expiration valve 19 may also be automatically adjusted by the control unit 21 during ongoing HFO ventilation to compensate for any deviation between the measured pressure profile and the desired pressure profile. To this end the control unit 21 may adjust the profile of the control current used to regulate the expiration valve 19, to thereby adjust one or more of the following parameters: the timing with which it is opened and closed; the degree of opening; the opening speed; the closing speed, and the force required to open the valve when closed (closing force). Although the embodiment illustrated in FIG. 4 and FIGS. 5A-5G involves active control of an expiration valve 17 to enhance the effect of the HFO ventilation, it should be appreciated that the expiration valve 19 and the control thereof is an advantageous but not required feature of the invention. It has been shown that both active inspiration and active expiration of the patient 3 can be achieved even without the use of the expiration valve 19.

If no controllable expiration valve 19 is used, it may be advantageous to equip the breathing apparatus 1 with some other means for preventing or limiting reverse flow of gas in the expiratory line 9. Such means could for example include a one-way valve preventing reverse flow in the expiration line (i.e. a flow towards the patient from the other side of the one-way valve). It has also been shown that a sufficient limitation of reverse flow in the expiration line is achieved by increasing the length of the expiratory line 9. Thus, it should be appreciated that the breathing apparatus 1 of the invention may comprise means for preventing or limiting a reverse flow of gas in the expiratory line 9 during the end of the active expiration phases, which means may include one or more of:

- a controllable expiration valve 19 arranged in a distal end of the expiratory line 9,
- a one-way valve (check valve) arranged in a distal end of the expiratory line 9, and
- a length of tubing extending the length of the expiratory line 9.

As understood by the skilled person, FIGS. 3A-3G and FIGS. 5A-5G are only schematic illustrations of flows and pressures in the patient circuit of the breathing apparatus 1. They are provided only to give the reader a simple explanation of the physical principles allowing true HFO ventilation to be provided to a patient 3 by means of fast regulation of an inspiration valve 17, without the use of ejectors, loudspeakers, pistons or any other means normally used in HFO ventilators of today to generate the negative pressure components of the oscillating pressure profile.

Figure 6:
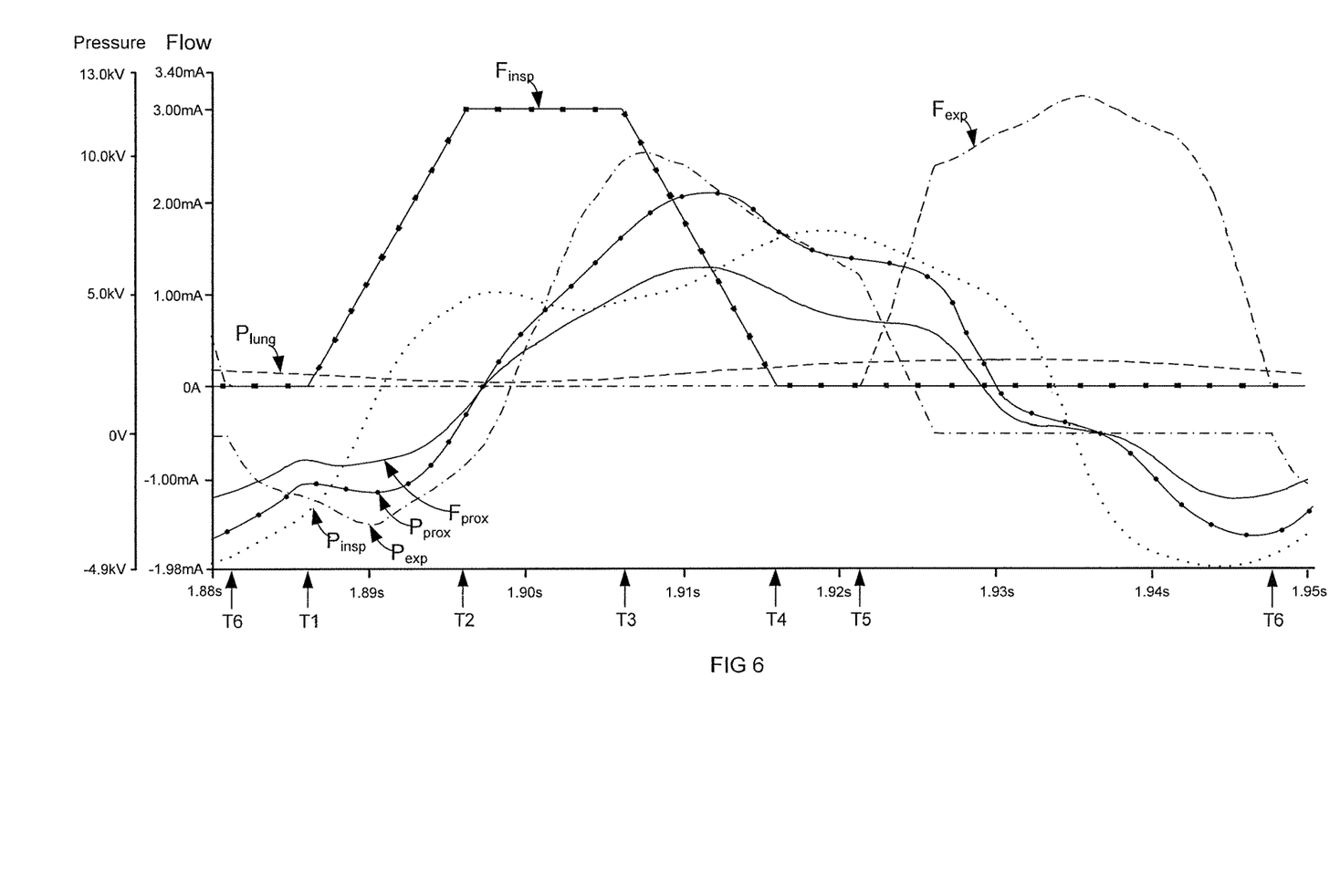
FIG. 6 illustrates in more detail the pressure and flow development in the patient circuit of a breathing apparatus providing HFO ventilation according to an exemplary embodiment of the invention.

A better understanding of the pressure and flow changes in the patient circuit 5, 9, 13 may be obtained by studying FIG. 6, illustrating the result of a simulation of the flow and pressure developments in the patient circuit during the proposed valve controlled HFO ventilation.

The simulation was made by simulating the inspiration valve 17 with a current generator, the compliance of the inspiratory line 5 with a capacitance, and the expiration valve 19 with a diode arranged on a proximal side of a voltage generator. The patient circuit was modelled by two 64 node RLC networks, one for the inspiratory line 5 and one for the expiratory line 9, with calculated component values. The patient lung was modelled by a resistor and a capacitance having component values making the lung model correspond to a lung of a neonatal patient. All other component values were selected so as to simulate the behaviour of the SERVO-i ventilator from Maquet Critical Care AB.

The simulation was made for HFO ventilation with a top flow rate of 180 lpm, an oscillation frequency of 15 Hz and a MAP of 25 mbar. The minimum flow rate (bias flow) was set to zero. This means that the simulation simulates HFO ventilation wherein the inspiration valve 17 oscillates between a top flow position at which the flow through the inspiration valve is 180 lpm and a completely closed position at which the flow through the inspiration valve is zero. In accordance with the capacity of the valve control mechanism of the Servo-i ventilator, the fall time from 180 lpm to zero flow was 10 ms, which yields a deceleration of the flow through the inspiration valve 17 of 18000 lpm/s. The model included use of an expiration valve 19 in order to prolong the active expiration phases of the patient, as described above with reference to FIG. 4 and FIGS. 5A-5G.

Some aspects having a positive impact on the HFO ventilation were not taken into account in the simulation. For example, the pressure increase in the patient circuit caused by the opening of the inspiration valve 17 exerts a force on the membrane of the inspiration valve 17, which force serves to increase the opening speed and hence the acceleration of flow through the valve even more. Likewise, when closing the inspiration valve 17, the negative pressure field 29 (see e.g. FIG. 3D) caused by the deceleration of the gas flow through the inspiration valve will exert a force on the membrane of the inspiration valve 17 serving to increase the closing speed and hence the deceleration of flow even more. These phenomenons were not modelled.

In FIG. 6, the following annotations are used for the different flows and pressures obtained as a result of the simulation:

$P_{prox}$: The proximal pressure. This is the pressure at the distal end of the common line 13 and corresponds to the pressure measured by the pressure sensor 16 (FIG. 1). This pressure is the pressure normally referred to when talking about pressure amplitudes and MAP of HFO ventilation.

$F_{prox}$: The proximal flow. This is the flow through the common line 13 of the patient connector 13, i.e. the flow towards the patient (positive flow) or away from the patient (negative flow). This flow corresponds to a flow measured by the flow sensor 15c (FIG. 1).

$P_{insp}$: The inspiratory line pressure. This is the pressure in the inspiratory line 5, at or near the inspiration valve 17. This pressure corresponds to a pressure that would have been measured by a pressure sensor co-located with the flow sensor 15a (FIG. 1).

$F_{insp}$: The inspiratory line flow. This is the flow through the inspiratory line 5, at or near the inspiration valve 17. This flow corresponds to a flow measured by the flow sensor 15a (FIG. 1).

$P_{exp}$: The expiratory line pressure. This is the pressure in the expiratory line 9, at or near the expiration valve 19. This pressure corresponds to a pressure that would have been measured by a pressure sensor co-located with the flow sensor 15b (FIG. 1).

$F_{exp}$: The expiratory line flow. This is the flow through the expiratory line 9, at or near the expiration valve 19. This flow corresponds to a flow measured by the flow sensor 15b (FIG. 1).

$P_{lung}$: The lung pressure. This is the lung pressure of the patient 3.

In FIG. 6, the y-axis shows flow in m³/s (1 A=1 m³/s, meaning that 1 mA equals 1 l/s or 60 lpm) and pressure in Pascal (1 V=1 Pa, meaning that 1 kV equals 10 cmH₂O). The x-axis shows time in seconds.

T1 indicates a point in time at which opening of the inspiration valve 17 is initiated, T2 a point in time at which the inspiration valve 17 reaches its most open position (the top flow position), T3 a point in time at which closing of the inspiration valve is initiated, and T4 a point in time at which the inspiration valve is fully closed. T5 indicates a point in time at which the expiration valve 19 is opened, and T6 a point in time at which the expiration valve 19 is closed.

As can be seen by studying the graph $P_{insp}$ in FIG. 6, the opening of the inspiration valve 17 causes a steep pressure increase in the inspiratory line. When the inspiration valve has reached its most open position the flow $F_{insp}$ through the inspiration valve stops to increase, which causes a temporary dip in the inspiratory line pressure $P_{insp}$ before starting to increase again when pressure increase due to the filling of the patient and patient circuit compliances becomes the dominant factor. Due to the speed of sound, the pressure wave is delayed between the inspiration valve 17 and the patient connector 11. As can be seen by studying the proximal pressure $P_{prox}$, the pressure at the patient connector 11 becomes negative shortly after the abrupt closing the inspiration valve 17. The simulation shows that a negative pressure swing having a maximum amplitude of approximately −40 cmH₂O is obtained in the proximal part of the patient circuit, which is more than enough to provide for active expiration of the patient 3. Furthermore it can be seen from a comparison between $F_{insp}$ and $F_{prox}$ that only a minor part of the flow through the inspiration valve 17 reaches the patient 3.

To obtain a negative pressure that is sufficient to provide for truly active expiration, the dynamics of the inspiration valve 17 and the profile of the control current applied to the inspiration valve by the control unit 21 should be such that the closing speed of the inspiration valve results in a mean rate of change in flow from the top flow rate to the minimum flow rate of at least 7200 lpm/s, more preferably 12000 lpm/s and even more preferably 18000 lpm/s. Furthermore, as previously mentioned, the magnitude of the negative pressure depends on the kinetic energy of the breathing gas pulses and hence the flow rate of the breathing gas through the inspiration valve. The higher the top flow rate through the inspiration valve 17, the higher the pressure swing of the oscillating pressure profile. Although the above simulation is made for a top flow rate of 180 lpm, a top flow rate of 30 lpm may be sufficient to provide for active expiration. Preferably, however, the top flow rate should be at least 60 lpm and even more preferably at least 120 lpm. Also, although the above simulation simulates a scenario in which the inspiration valve 17 oscillates between the top flow position and a completely closed position in which the flow rate through the valve is zero, a sufficient negative pressure may still be obtained with a small bias flow through the inspiration valve 17 when in its most closed position. This bias flow should not exceed 4 lpm and should preferably not exceed 1 lpm.

Figure 7:
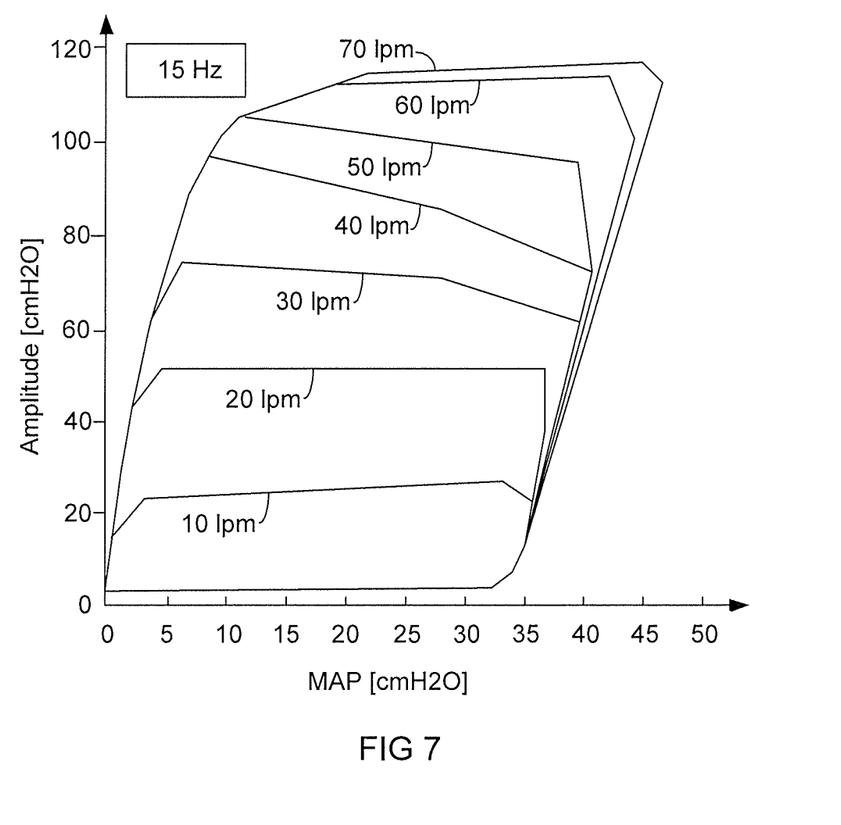
FIG. 7 illustrates MAP and pressure amplitude coverage of the inventive HFO ventilation for different mean flow rates at 15 Hz.

FIG. 7 is a diagram showing the proximal mean pressure and the proximal pressure amplitude coverage of the inventive valve controlled HFO ventilation at an exemplary frequency of 15 Hz for different mean flow rates. As mentioned above, the proximal mean pressure and the proximal pressure amplitude are measured by pressure sensor 16 in FIG. 1 and correspond to what is normally referred to as the MAP and pressure amplitude, respectively, in the context of HFO ventilation. As understood by the skilled person, the mean flow rate is the mean flow through the inspiration valve 17 during a period of the HFO ventilation, during which the inspiration valve 17 goes from the minimum flow position to the top flow position and back again. In FIG. 7, the inner loop shows the MAP and pressure amplitude coverage at a mean flow rate of 10 lpm, the next loop shows the MAP and pressure amplitude coverage at a mean flow rate of 20 lpm, and so on, up to the outer loop which shows the MAP and pressure amplitude coverage at a mean flow rate of 70 lpm.

We claim as our invention:

1. A breathing apparatus for providing high frequency oscillatory ventilation [HFO] to a patient by supplying breathing gas to the patient according to an oscillating pressure profile oscillating between a positive pressure and a negative pressure, comprising:
    a patient circuit including an inspiratory line for conveying breathing gas to the patient, and an expiratory line for conveying gas away from the patient;
    a controllable inspiration valve for regulating a flow of pressurised breathing gas into the inspiration line;
    a control computer configured to control the inspiration valve and to generate positive and negative pressure components of the oscillating pressure profile by controlling the inspiration valve to oscillate between a top flow position in which the flow of breathing gas through the inspiration valve assumes a top flow value, and a minimum flow position in which the flow through the inspiration valve assumes a minimum flow value, wherein the positive pressure components are generated by an opening of the inspiration valve to the top flow position, allowing breathing gas to flow through the inspiration valve at the top flow value, and the negative pressure components are generated by a closing of the inspiration valve to the minimum flow position causing a deceleration of the breathing gas flow from the top flow value to the minimum flow value; and
    an electronically controlled expiration valve regulating the flow of gas through the expiratory line, wherein the control computer is configured to cause the expiration valve to oscillate with an oscillation pattern that is out of phase with the oscillation pattern of the inspiration valve,
    wherein the control computer is configured to, in each period of the HFO ventilation, close the expiration valve while the pressure in the patient circuit is negative, and open the inspiration valve with a time delay after closing the expiration valve that produces an increase in the duration of active expiration.

2. The breathing apparatus according to claim 1, wherein the control computer is configured to cause the inspiration valve to go from the top flow position to the minimum flow position with a speed causing a mean rate of change in flow from the top flow value to the minimum flow value of at least 7200 lpm/s.

3. The breathing apparatus according to claim 1, wherein the top flow value is at least 30 lpm.

4. The breathing apparatus according to claim 1, wherein the minimum flow value is at most 4 lpm.

5. The breathing apparatus according to claim 1, wherein the minimum flow value is at most 1 lpm.

6. The breathing apparatus according to claim 1, further comprising a mechanism preventing a reverse flow of gas in the expiratory line.

7. The breathing apparatus according to claim 6, wherein the mechanism for preventing a reverse flow of gas in the expiratory line comprises one of an expiration valve, a mechanical one-way valve, and a length of tubing extending the length of the expiratory line.

8. The breathing apparatus according to claim 6, wherein the mechanism preventing a reverse flow of gas in the expiratory line includes an expiration valve.

9. The breathing apparatus according to claim 1, wherein both the positive and negative pressure components of the oscillating pressure profile are exclusively generated by the oscillating inspiration valve.

10. The breathing apparatus according to claim 1,
wherein the minimum flow position is a closed or nearly closed position at which the flow through the inspiration valve is zero or nearly zero.

11. The breathing apparatus according to claim 1, wherein the negative pressure components are generated only by use of kinetic energy of breathing gas pulses injected through the inspiration valve.

12. A method for providing FIFO ventilation to a patient by supplying breathing gas to the patient according to an oscillating pressure profile oscillating between a positive pressure and a negative pressure, comprising the steps of:
supplying pressurised breathing gas to the patient via a controllable inspiration valve in an inspiratory line of a patient circuit;
conveying gas away from the patient via an expiratory line of the patient circuit;
generating positive and negative pressure components of the oscillating pressure profile by operating the inspiration valve to oscillate between a top flow position in which the flow of breathing gas through the inspiration valve assumes a top flow value, and a minimum flow position in which the flow through the inspiration valve assumes a minimum flow value, wherein the positive pressure components are generated by an opening of the inspiration valve to the top flow position, allowing breathing gas to flow through the inspiration valve at the top flow value, and the negative pressure components are generated by a closing of the inspiration valve to the minimum flow position causing a deceleration of the breathing gas flow from the top flow value to the minimum flow value;
operating an expiration valve in the expiratory line to oscillate with an oscillation pattern that is out of phase with the oscillation pattern of the inspiration valve; and
in each period of the HFO ventilation, closing the expiration valve while the pressure in the patient circuit is negative, and opening the inspiration valve with a time delay after closing the expiration valve that produces an increase in the duration of active expiration during expiration phases.

13. The method according to claim 12, further comprising operating the inspiration valve to go from the top flow position to the minimum flow position with a speed causing a mean rate of change in flow from the top flow value to the minimum flow value of at least 7200 lpm/s.

14. The method according to claim 12, wherein the top flow value is at least 30 lpm.

15. The method according to claim 12, wherein the minimum flow value is at most 4 lpm.

16. The method according to claim 12, wherein the minimum flow value is at most 1 lpm.

17. The method according to claim 12, further comprising preventing a reverse flow of gas in the expiratory line.

18. The method according to claim 12, further comprising generating both the positive and negative pressure components of the oscillating pressure profile exclusively by operating the oscillating inspiration valve.

19. The method according to claim 12,
wherein the minimum flow position is a closed or nearly closed position at which the flow through the inspiration valve is zero or nearly zero.

20. The method according to claim 12, wherein the negative pressure components are generated only by use of kinetic energy of breathing gas pulses injected through the inspiration valve.

21. A non-transitory, computer-readable data storage medium encoded with programming instructions, the storage medium being loaded into a control computer of a breathing apparatus, the breathing apparatus comprising a patient circuit that includes an inspiratory line for conveying breathing gas to a patient and an expiratory line for conveying gas away from the patient, and an inspiration valve for regulating a flow of pressurized breathing gas into the inspiration line, the breathing apparatus being configured to provide high frequency oscillatory ventilation to the patient by supplying breathing gas to the patient according to an oscillating pressure profile that oscillates between a positive pressure and a negative pressure, and the programming instructions causing the control computer to:
operate the inspiration valve to generate positive and negative pressure components of the oscillating pressure profile by causing the inspiration valve to oscillate between a top flow position in which the flow of breathing gas through the inspiration valve assumes a top flow value, and a minimum flow position in which the flow through the inspiration valve assumes a minimum flow value, wherein the positive pressure components are generated by an opening of the inspiration valve to the top flow position, allowing breathing gas to flow through the inspiration valve at the top flow value, and the negative pressure components are generated by a closing of the inspiration valve to the minimum flow position causing a deceleration of the breathing gas flow from the top flow value to the minimum flow value; and
operate an expiration valve in the expiratory line to oscillate with an oscillation pattern that is out of phase with the oscillation pattern of the inspiration valve,
wherein, in each period of the HFO ventilation, the expiration valve is closed while the pressure in the patient circuit is negative, and the inspiration valve is opened with a time delay after closing the expiration valve that produces an increase in the duration of active expiration during expiration phases.

22. A breathing apparatus for providing high frequency oscillatory ventilation [FIFO] to a patient by supplying breathing gas to the patient according to an oscillating pressure profile oscillating between a positive pressure and a negative pressure, comprising:
- a patient circuit including an inspiratory line for conveying breathing gas to the patient, and an expiratory line for conveying gas away from the patient;
- a controllable inspiration valve for regulating a flow of pressurised breathing gas into the inspiration line;
- a control computer configured to control the inspiration valve and to generate positive and negative pressure components of the oscillating pressure profile by controlling the inspiration valve to oscillate between a top flow position in which the flow of breathing gas through the inspiration valve assumes a top flow value, and a minimum flow position in which the flow through the inspiration valve assumes a minimum flow value, wherein the positive pressure components are generated by an opening of the inspiration valve to the top flow position, allowing breathing gas to flow through the inspiration valve at the top flow value, and the negative pressure components are generated by a closing of the inspiration valve to the minimum flow position causing a deceleration of the breathing gas flow from the top flow value to the minimum flow value; and
- an electronically controlled expiration valve regulating the flow of gas through the expiratory line, wherein the control computer is configured to cause the expiration valve to oscillate with an oscillation pattern that is out of phase with the oscillation pattern of the inspiration valve,
- wherein the control computer is configured to, in each period of the HFO ventilation, keep the expiration valve closed when the inspiration valve is open, and open the expiration valve with a time delay after closing the inspiration valve that produces an increase in the flow of breathing gas into the airways of the patient during inspiration phases.

23. A method for providing HFO ventilation to a patient by supplying breathing gas to the patient according to an oscillating pressure profile oscillating between a positive pressure and a negative pressure, comprising the steps of:
- supplying pressurised breathing gas to the patient via a controllable inspiration valve in an inspiratory line of a patient circuit;
- conveying gas away from the patient via an expiratory line of the patient circuit;
- generating positive and negative pressure components of the oscillating pressure profile by operating the inspiration valve to oscillate between a top flow position in which the flow of breathing gas through the inspiration valve assumes a top flow value, and a minimum flow position in which the flow through the inspiration valve assumes a minimum flow value, wherein the positive pressure components are generated by an opening of the inspiration valve to the top flow position, allowing breathing gas to flow through the inspiration valve at the top flow value, and the negative pressure components are generated by a closing of the inspiration valve to the minimum flow position causing a deceleration of the breathing gas flow from the top flow value to the minimum flow value;
- operating an expiration valve in the expiratory line to oscillate with an oscillation pattern that is out of phase with the oscillation pattern of the inspiration valve; and
- in each period of the HFO ventilation, keeping the expiration valve closed when the inspiration valve is open, and opening the expiration valve with a time delay after closing the inspiration valve that produces an increase in the flow of breathing gas into the airways of the patient during inspiration phases.

24. A non-transitory, computer-readable data storage medium encoded with programming instructions, the storage medium being loaded into a control computer of a breathing apparatus, the breathing apparatus comprising a patient circuit that includes an inspiratory line for conveying breathing gas to a patient and an expiratory line for conveying gas away from the patient, and an inspiration valve for regulating a flow of pressurized breathing gas into the inspiration line, the breathing apparatus being configured to provide high frequency oscillatory ventilation to the patient by supplying breathing gas to the patient according to an oscillating pressure profile that oscillates between a positive pressure and a negative pressure, and the programming instructions causing the control computer to:
- operate the inspiration valve to generate positive and negative pressure components of the oscillating pressure profile by causing the inspiration valve to oscillate between a top flow position in which the flow of breathing gas through the inspiration valve assumes a top flow value, and a minimum flow position in which the flow through the inspiration valve assumes a minimum flow value, wherein the positive pressure components are generated by an opening of the inspiration valve to the top flow position, allowing breathing gas to flow through the inspiration valve at the top flow value, and the negative pressure components are generated by a closing of the inspiration valve to the minimum flow position causing a deceleration of the breathing gas flow from the top flow value to the minimum flow value; and
- operate an expiration valve in the expiratory line to oscillate with an oscillation pattern that is out of phase with the oscillation pattern of the inspiration valve,
- wherein, in each period of the HFO ventilation, the expiration valve is kept closed when the inspiration valve is open, and the expiration valve is opened with a time delay after closing the inspiration valve that produces an increase in the flow of breathing gas into the airways of the patient during inspiration phases.

* * * * *